United States Patent [19]
Gull et al.

[11] Patent Number: 5,133,903
[45] Date of Patent: Jul. 28, 1992

[54] PROCESS FOR THE PREPARATION OF ω-ENECARBOXYLIC ACID ESTERS

[75] Inventors: Reinhold Gull; Thomas Keil, both of Marl, Fed. Rep. of Germany

[73] Assignee: Huels Aktiengesellschaft, Marl, Fed. Rep. of Germany

[21] Appl. No.: 316,937

[22] Filed: Feb. 28, 1989

[30] Foreign Application Priority Data

Apr. 13, 1988 [DE] Fed. Rep. of Germany ....... 3812184

[51] Int. Cl.$^5$ ................ C07C 67/38; C07C 69/533; C07C 69/58
[52] U.S. Cl. .................................. 554/130; 568/342; 554/131; 560/114
[58] Field of Search .............. 260/410.9 R, 413

[56] References Cited

U.S. PATENT DOCUMENTS 4,481,147 11/1984 Hofmann ............... 260/410.9 A

OTHER PUBLICATIONS

J. Falbe, *Synthesen mit Kohlenmonoxid*, pp. 102-103 (1967).

*Primary Examiner*—Vivian Garner
*Attorney, Agent, or Firm*—Oblon, Spivak, McClelland, Maier & Neustadt

[57] ABSTRACT

Hydrocarboxyalkylation of α,ω-dienes with carbon monoxide and an alcohol in the presence of a cobalt compound and a tertiary amine gives ω-enecarboxylic acid esters with high selectivity and in good yields.

14 Claims, No Drawings

PROCESS FOR THE PREPARATION OF ω-ENECARBOXYLIC ACID ESTERS

BACKGROUND OF THE INVENTION

1. Field of the Invention

The present invention relates to a process for the preparation of ω-enecarboxylic acid esters by hydrocarboxyalkylation of α,ω-dienes.

2. Discussion of the Background

In the context of the present invention, ω-enecarboxylic acid esters are compounds which possess a terminal carbon-carbon double bond at one end of an alkylene chain and an ester group at the other end of the alkylene chain.

ω-Enecarboxylic acid esters are valuable intermediates for the production of detergents, lubricants, emulsifiers, plasticizers, alkyd resins, polyamides, and perfumes and flavors.

ω-Enecarboxylic acids with up to 13 carbon atoms can be synthesized from small structural units in several steps by the method of A. Seher, *Fette-Seifen-Anstrichmittel*, 58, 1077 (1956). ω-Enecarboxylic acids can be produced from ω-eneketocarboxylic acids by Wolff-Kishner reduction according to the method of S. Huenig and W. Eckardt, *Chemische Berichte*, 95, 2498 (1962). The starting materials for this reaction are not available in industrial quantities. Furthermore, the double bond is partly isomerized during the reduction. Neither method has attained industrial importance.

According to DE-A 36 09 138 and DE-A 36 09 139, ω-enecarboxylic acid esters with chains of 5 to 7 carbon atoms can be obtained by cleaving lactones. In this method, which is suitable only for preparing short-chained ω-enecarboxylic acid esters, the double bond is partly isomerized. Because of this isomerization, products with an internal double bond are also synthesized in substantial quantities.

According to DE-A 30 24 884, unsaturated $C_9$-carboxylic acids can be prepared by carboxylative dimerization of 1,3-butadiene with carbon dioxide in the presence of palladium compounds, phosphine, and formic acid. However, the 2-ethylidenehept-6-enecarboxylic acid obtained in the mixture has both a terminal and an internal double bond and a branch.

Olefins can be hydrocarboxyalkylated with carbon monoxide in the presence of alcohols by the method of J. Falbe, *Synthesen mit Kohlenmonoxid*, 102 (1967). Thus, unsaturated monocarboxylic acid esters can be prepared from 1,5-cyclooctadiene on Pd/HCl, while the saturated monocarboxylic acids are always formed on cobalt catalysts. 1,5-Hexadiene reacts with cyclization on a palladium catalyst.

No process for the hydrocarboxyalkylation of α,ω-dienes with the formation of ω-enecarboxylic acid esters is described by J. Falbe.

Thus, there is a need for a process to prepare ω-enecarboxylic acid esters from economical, simple starting compounds which are available in large quantities.

In particular, there is a need for a process to prepare largely unbranched ω-enecarboxylic acid esters from readily available starting materials.

SUMMARY OF THE INVENTION

Accordingly, it is an object of the present invention to provide a process for the production of ω-enecarboxylic acid esters from economical, simple starting materials which are available in large quantities.

It is another object of the present invention to provide a process for the production of largely unbranched ω-enecarboxylic acid esters from readily available starting materials.

These and other objects which will become apparent in the course of the following detailed description have been achieved by hydrocarboxyalkylating α,ω-dienes having 5 to 20 carbon atoms with carbon monoxide in the presence of a cobalt compound and a tertiary amine in an alcohol at 100° to 200° C. and 150 to 350 bar.

The production of ω-enecarboxylic acid esters by this method is surprising, since the α,ω-dienes and ω-enecarboxylic acid esters have double bonds with about the same reactivity.

DETAILED DESCRIPTION OF THE PREFERRED EMBODIMENTS

α,ω-Dienes with 5 to 20 carbon atoms are suitable starting materials for the present hydrocarboxyalkylation. α,ω-Dienes with 8 to 16 carbon atoms are preferred starting materials.

A suitable cobalt compound is cobalt tetracarbonyl hydride, $HCo(CO)_4$. Cobalt salts such as cobalt(II) acetate, naphthenate, stearate, carbonate, or chloride, cobalt oxides, or cobalt carbonyls such as dicobalt octacarbonyl can also be used. In addition to carbon monoxide, these cobalt compounds require 0.1 to 10 mole % hydrogen based on the moles of carbon monoxide in the initial phase of the hydrocarboxyalkylation. Under the present reaction conditions of 100° to 200° C. and 150 to 350 bar, cobalt tetracarbonyl hydride is formed, which is presumably the actual catalytically active compound. The formation of cobalt tetracarbonyl hydride is generally complete after about half an hour.

0.5 to 5 mole % of cobalt compound is preferably used, based on the α,ω-diene used.

Pyridine and pyridines which are not alkylated in the ortho position, such as 3- and 4-picoline, 3,4- and 3,5-lutidine, and 3- and 4-ethylpyridine are suitable tertiary amines that act as promoters. Pyridine, 4-picoline, and mixtures of them are preferred. The molar ratio of tertiary amine to cobalt compound is preferably 2:1 to 300:1.

Alcohols with 1 to 6 carbon atoms such as methanol, ethanol, isopropanol, butanol, or hexanol are generally useful as solvents and reagents. Methanol is preferred. The molar ratio of α,ω-diene to alcohol is preferably 1:1 to 1:4.

The present process may be carried out in any suitable apparatus, such as an autoclave. A temperature of 100° to 200° C. and a pressure of 150 to 350 bar are suitable. A temperature of 120° to 160° C. and a pressure of 200 to 300 bar are preferred.

The present process represents a general method for being able to prepare ω-enecarboxylic acid esters from α,ω-dienes by hydrocarboxyalkylation. Although the starting material and final products both have double bonds with about the same reactivity, ω-enecarboxylic acid esters are obtained with high selectivity and in good yields. The selectivity of the present process based on conversion is approximately 70 to 90%.

In addition, the present process provides ω-enecarboxylic acid esters with high linearity, that is usually above 90%. The by-products formed are predominantly ω-ene-α-methylcarboxylic acid esters.

In the present process, the terminal double bond is not isomerized, and no products with an internal double bond are obtained. The present process does not require any precious metal catalysts, and simple starting materials available in large quantities can be used.

Other features of the present invention will become apparent in the course of the following exemplary embodiments which are given for illustration and are not intended to be limiting thereof.

EXAMPLES

In the examples, a 5-liter VA steel autoclave with magnetic stirrer, temperature control, and pressure control is used in each case. The reaction components $\alpha,\omega$-diene, alcohol, cobalt compound, and amine are loaded and brought to the reaction temperature. Hydrogen is then introduced under pressure, whereupon the overall pressure is raised by introducing carbon monoxide under pressure. The pressure drop during the reaction is compensated for by constant introduction of carbon monoxide.

After completion of the hydrocarboxyalkylation, the mixture is cooled to room temperature and depressurized. The composition of the reaction product is determined by gas chromatography. The $\omega$-enecarboxylic acid ester is isolated by fractional distillation.

In the examples, percentages in each case are given in wt. %.

EXAMPLE 1

Starting materials:
772.2 g (9.4 moles) 1,5-hexadiene
451.8 g (14.1 moles) methanol
743.5 g (9.4 moles) pyridine
23.4 g (0.094 moles) Co(II) acetate
Reaction conditions: $T=140°$ C., $P_{H2}=10$ bar (initial), $P_{tot}=280$ bar, $t=18$ h.

Obtained at a conversion of 24.6% based on the 1,5-hexadiene used are:
16.8% methyl $\omega$-heptenoate
2.4% dimethyl octanedioate
5.4% 2,5-dimethylcyclopentanone

EXAMPLE 2

Starting materials:
870.6 g (7.9 moles) 1,7-octadiene
632.8 g (19.8 moles) methanol
441.4 g (4.74 moles) 4-picoline
59.0 g (0.237 moles) Co(II) acetate
Reaction conditions: $T=140°$ C., $P_{H2}=10$ bar (initial), $P_{tot}=280$ bar, $t=12$ h.

Obtained at a conversion of 36.8% based on the 1,7-octadiene used are:
32.8% methyl $\omega$-nonenoate
3.4% dimethyl decanedioate
0.6% 2-methyl-5-n-propylcyclopentanone

EXAMPLE 3

Starting materials:
914.7 g (8.3 moles) 1,7-octadiene
664.8 g (20.8 moles) methanol
347.8 g (3.7 moles) 4-picoline
62.0 g (0.25 moles) Co(II) acetate
Reaction conditions: $T=140°$ C., $P_{H2}=10$ bar (initial), $P_{tot}=280$ bar, $t=6$ h.

Obtained at a conversion of 32.2% based on the 1,7-octadiene used are:
29.2% methyl $\omega$-nonenoate
2.4% dimethyl decanedioate
0.5% 2-methyl-5-n-propylcyclopentanone

EXAMPLE 4

The procedure of Example 3 is followed, with the exception that the reaction time is extended to 9 h.

Obtained at a conversion of 39.7% based on the 1,7-octadiene used are:
34.6% methyl $\omega$-nonenoate
4.1% dimethyl decanedioate
1.0% 2-methyl-5-n-propylcyclopentanone

EXAMPLE 5

Starting materials:
1,036.9 g (7.5 moles) 1,9-decadiene
360.5 g (11.25 moles) methanol
593.3 g (7.5 moles) pyridine
18.7 g (0.075 moles) Co(II) acetate
Reaction conditions: $T=140°$ C., $P_{H2}=10$ bar (initial), $P_{tot}=280$ bar, $t=18$ h.

Obtained at a conversion of 37.6% based on the 1,9-decadiene used are:
31.6% methyl $\omega$-undecenoate
4.1% dimethyl dodecanedioate
1.2% 2-methyl-5-n-pentylcyclopentanone

EXAMPLE 6

Starting materials:
925.7 g (8.4 moles) 1,7-octadiene
812.7 g (17.6 moles) ethanol
117.3 g (1.26 moles) 4-picoline
148.5 g (0.25 moles) Co(II) naphthenate
Reaction conditions: $T=130°$ C., $P_{H2}=5$ bar (initial), $P_{tot}=200$ bar, $t=1$ h.

Obtained at a conversion of 37.4% based on the 1,7-octadiene used are:
31.8% ethyl $\omega$-nonenoate
4.4% diethyl decanedioate
1.2% 2-methyl-5-n-propylcyclopentanone

EXAMPLE 7

Starting materials:
683.2 g (6.2 moles) 1,7-octadiene
1,148.9 g (15.5 moles) n-butanol
73.6 g (0.93 moles) pyridine
109.6 g (0.19 moles) Co(II) naphthenate
Reaction conditions: $T=130°$ C., $P_{H2}=10$ bar (initial), $P_{tot}=280$ bar, $t=1$ h.

Obtained at a conversion of 43.7% based on the 1,7-octadiene used are:
35.9% butyl $\omega$-nonenoate
5.9% dibutyl decanedioate
1.9% 2-methyl-5-n-propylcyclopentanone Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the preparation of a $\omega$-enecarboxylic acid ester, comprising reacting (a) an $\alpha,\omega$-diene with 5 to 20 carbon atoms, (b) carbon monoxide, and (c) an alcohol in the presence of a cobalt compound and a tertiary amine at a temperature of 120° to 160° C. and a pressure of 150 to 350 bar.

2. The process of claim 1, wherein said cobalt compound is one member selected from the group consisting of cobalt tetracarbonyl hydride, cobalt salts, cobalt oxides, and cobalt carbonyls.

3. The process of claim 2, wherein said cobalt salt is one member selected from the group consisting of cobalt (II) acetate, cobalt (II) naphthenate, cobalt (II) stearate, cobalt (II) carbonate, and cobalt (II) chloride.

4. The process of claim 1, wherein said tertiary amine is one member selected from the group consisting pyridine and pyridines which are not alkylated in the ortho position.

5. The process of claim 4, wherein said pyridine which is not alkylated in the ortho position is one member selected from the group consisting of 3-picoline, 4-picoline, 3,4,-lutidine, 3,5-lutidine, 3-ethylpyridine, and 4-ethylpyridine.

6. The process of claim 1, wherein said tertiary amine is one member selected from the group consisting of pyridine and 4-picoline.

7. The process of claim 1, wherein said alcohol has 1 to 6 carbon atoms.

8. The process according to claim 7, wherein said alcohol is one member selected from the group consisting of methanol, ethanol, isopropanol, butanol and hexanol.

9. The process of claim 8, wherein said alcohol is methanol.

10. The process of claim 1, wherein said pressure is 200 to 300 bar.

11. The process of claim 1, wherein said $\alpha,\omega$-diene has 8 to 16 carbon atoms.

12. The process of claim 1, wherein said cobalt compound is present in an amount of from 0.5 to 5 mole % based on the amount of said $\alpha,\omega$-diene.

13. The process of claim 1, wherein the molar ratio of said tertiary amine to said cobalt compound is from 2:1 to 300:1.

14. The process of claim 1, wherein the molar ratio of said $\alpha,\omega$-diene to said alcohol is from 1:1 to 1:4.

* * * * *